(12) United States Patent
Denardo et al.

(10) Patent No.: US 7,288,112 B2
(45) Date of Patent: Oct. 30, 2007

(54) INTRAVASCULAR FLOW MODIFIER AND REINFORCEMENT DEVICE

(75) Inventors: Andrew J. Denardo, Carmel, IN (US); David A. Ferrera, Manhattan Beach, CA (US); Peter Wilson, Foster City, CA (US); Lok A. Lei, San Jose, CA (US)

(73) Assignee: Micrus Endovascular Corporation, San Jose, CA (US)

( * ) Notice: Subject to any disclaimer, the term of this patent is extended or adjusted under 35 U.S.C. 154(b) by 293 days.

(21) Appl. No.: 11/083,618

(22) Filed: Mar. 18, 2005

(65) Prior Publication Data

US 2005/0165473 A1  Jul. 28, 2005

Related U.S. Application Data

(63) Continuation of application No. 10/712,887, filed on Nov. 12, 2003, now Pat. No. 6,878,163, which is a continuation of application No. 09/590,793, filed on Jun. 8, 2000, now Pat. No. 6,656,218, which is a continuation-in-part of application No. 09/122,243, filed on Jul. 24, 1998, now Pat. No. 6,165,194.

(51) Int. Cl.
*A61F 2/06* (2006.01)
*A61M 29/00* (2006.01)

(52) U.S. Cl. ...................... 623/1.15; 606/108
(58) Field of Classification Search ...... 623/1.11–1.22; 606/108, 191–198
See application file for complete search history.

(56) References Cited

U.S. PATENT DOCUMENTS

| 5,643,339 | A | * | 7/1997 | Kavteladze et al. | ....... 623/1.22 |
| 5,830,229 | A | * | 11/1998 | Konya et al. | ................ 606/198 |
| 5,895,398 | A | | 4/1999 | Wensel et al. | |
| 6,059,825 | A | | 5/2000 | Hobbs et al. | |
| 6,063,113 | A | | 5/2000 | Kavteladze et al. | |
| 6,485,524 | B2 | * | 11/2002 | Strecker | .................... 623/1.15 |

FOREIGN PATENT DOCUMENTS

WO          WO 01/08743          2/2001

* cited by examiner

*Primary Examiner*—Vy Q. Bui
(74) *Attorney, Agent, or Firm*—Fulwider Patton LLP

(57) ABSTRACT

An intravascular flow modifier and vascular reinforcement for treatment of aneurysms is formed of one or more loops of wire of resilient material formed into a series of transverse loops and longitudinal connecting sections to configure an essentially cylindrical reinforcement device that still allows, if desired, access to the neck of an aneurysm for insertion of embolic coils and the like. The proximal and distal regions of the sinusoidal loops may be more tightly coiled than the intermediate regions of the loops, or may have a larger diameter than the intermediate regions. The intravascular flow modifier and vascular reinforcement device can be provided with an outer covering that can be formed as a fiber, and can be woven, or can be formed as a ribbon wound about the intravascular flow modifier and vascular reinforcement device. The wire of resilient material can also be coated with a hydrophilic material. One or more round or oval intermediate loops extending radially outward may also be provided. An apparatus for removing clots may also be formed from one or more loops of wire of resilient material in a hollow conical shape non-detachably joined to a deployment device, to trap and hold clots within a vessel.

9 Claims, 5 Drawing Sheets

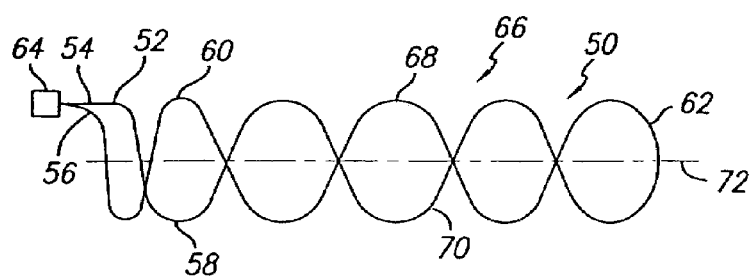
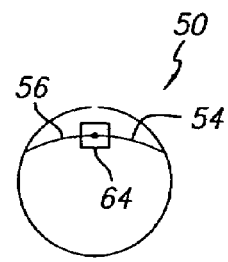
FIG. 9
FIG. 10
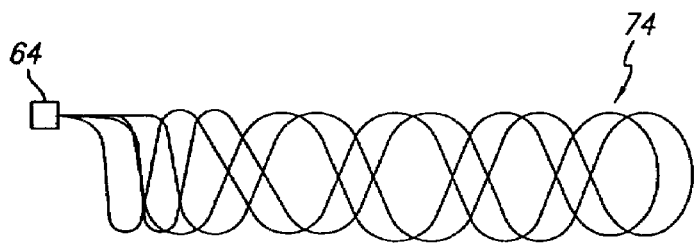
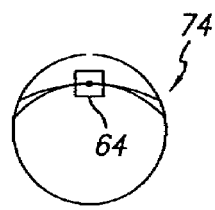
FIG. 11
FIG. 12
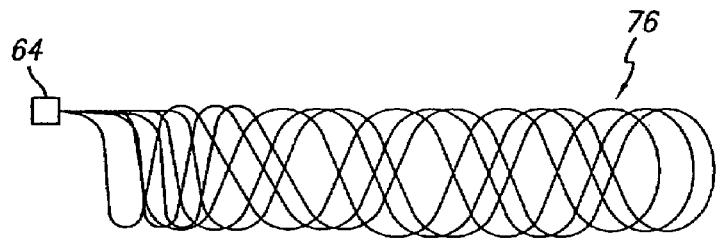
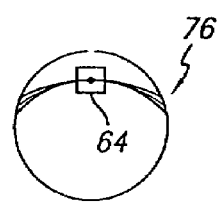
FIG. 13
FIG. 14
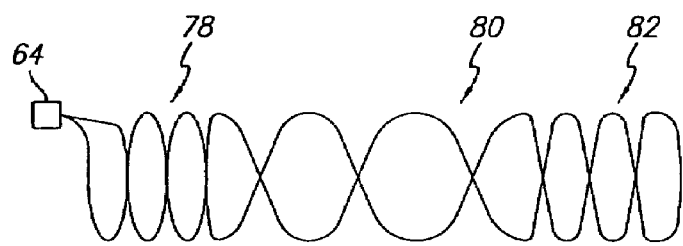
FIG. 15

INTRAVASCULAR FLOW MODIFIER AND REINFORCEMENT DEVICE

RELATED APPLICATIONS

This is a continuation of Ser. No. 10/712,887, filed Nov. 12, 2003, now Pat. No. 6,878,163, which is a continuation of Ser. No. 09/590,793 filed Jun. 8, 2000, now Pat. No. 6,656,218, which is a continuation-in-part of Ser. No. 09/122,243 filed Jul. 24, 1998, now Pat. No. 6,165,194.

BACKGROUND OF THE INVENTION

1. Field of the Invention

The present invention relates to an intravascular flow modifier and reinforcement device for use within a body vessel, and more particularly, for a device to be used in combination with vasoocclusive devices placed in an aneurysm for the purpose of occluding an aneurysm, whereby the invention provides reinforcement for the area of the blood vessel in the vicinity of the aneurysm.

2. Description of the Related Art

The progress of the medical arts related to treatment of vascular malformations has dramatically improved with the availability of intravascular devices capable of operating entirely within the vasculature. Thus, many highly invasive surgical procedures and inoperable conditions have been treated by the use of an expanding number of devices and procedures designed for those purposes. One particularly useful development in the medical arts has been the ability to treat defects in relatively small arteries and veins, such as those in the neurovascular system, by use of a micro-catheter and the placement of embolic coils and the like in areas where the malformation is likely to cause or has already caused a rupture in the blood vessel. More specifically, it has been found that the treatment of aneurysms by such devices and procedures allows the medical practitioner to avoid otherwise risky medical procedures. For example, when the placement of the defect is in the brain, a great deal of difficulty is presented to treatment of small defects in the blood vessels with conventional surgical techniques. For these reasons, the progress in development of devices to treat such defects has been encouraged and has produced useful results in a wide variety of patients.

One aspect of these surgical treatments is that an aneurysm or other malformation is symptomatic of a general weakening of the vasculature in the area containing the aneurysm, and mere treatment of the aneurysm does not necessarily prevent a subsequent rupture in the surrounding area of the vessel. Moreover, it is often desirable to provide a means to prevent the migration of the vasoocclusive devices, such as coils and the like, out of the aneurysm in the event that the aneurysm has a relatively large neck to dome ratio.

Stents, which are tubular reinforcements inserted into a blood vessel to provide an open path within the blood vessel, have been widely used in intravascular angioplasty treatment of occluded cardiac arteries. In such a case, the stent is inserted after an angioplasty procedure or the like in order to prevent restenosis of the artery. In these applications, the stents are often deployed by use of inflatable balloons, or are self-expanding, forcing the stent open, thereby reinforcing the artery wall in the clear through-path in the center of the artery after the angioplasty procedure to prevent restenosis. While such procedures may be useful in certain aspects of vascular surgery in which vasoocclusive devices are used, the weakness of the vasculature and the inaccessibility of the interior of the aneurysm from the vessel after the placement of such a stent, places limits on the applicability of such stents in procedures to repair aneurysms, particularly neurovascular aneurysms. Furthermore, the use of placement techniques, such as balloons or self-expanding mechanical devices of the type often found to be useful in cardiac surgery are relatively less useful in vasoocclusive surgery, particularly when tiny vessels, such as those found in the brain, are to be treated. For these reasons, it would be helpful if a device were available which was compatible with new techniques in vasoocclusive treatment of aneurysms and provides selective reinforcement in the vicinity of the artery, while avoiding any unnecessary trauma or risk of rupture to the blood vessel. The present invention provides these and other advantages.

SUMMARY OF THE INVENTION

Briefly, and in general terms, the invention relates to a three-dimensional wire intravascular flow modifier which is formed of superelastic or shape memory material, which, in its deployed configuration comprises a series of circumferential loops connected by longitudinal portions proceeding in a multiple loop fashion from two free ends of the wire to a closed end loop of the wire. Upon deployment, the device is placed within the vasculature so that it extends from a position proximal to a position distal of the aneurysm to be treated. The device may be arranged so that an open portion of the loop straddles the neck of the aneurysm to allow placement of embolic coils and the like through the opening into the aneurysm. Prior to placement, the device is deformed into a linear form and placed within a microcatheter, which is used to position the distal end of the device so that the device is pushed out of the micro-catheter by means of a pusher and detached from the pusher by a variety of means to complete placement of the device. After placement of the device, the pusher and catheter are withdrawn.

In a presently preferred method of manufacture of the invention, a single piece of shape memory or superelastic alloys such as nickel titanium alloy, is wound over an essentially cylindrical mandrel into which are formed channels representing the progressive loop configuration of the invention. Alternatively, the mandrel may be cylindrical with pegs inserted in positions representing transitions between the circumferential loops and the longitudinal portions of the wire. A single wire is best wound progressively down the mandrel forming loops and longitudinal transitions until a desired length of the device is reached, at which point the path is retraced similarly to the position at which the device was begun on the mandrel. The wire can then be heat treated on the mandrel to create a shape memory or treated to reach a superelastic state. Thereafter, the device can be taken off of the mandrel and stretched to be inserted into a micro-catheter prior to insertion into the vasculature. The configuration of the present invention provides important advantages over prior art devices in that it eliminates the necessity for balloon or mechanical placement devices which can cause unnecessary trauma to the delicate vasculature which has already been damaged by the presence of the aneurysm. For this reason, the invention is particularly useful to cover and reinforce large neck aneurysms. The presence of the longitudinal portion of the coil dramatically improves the pushability of the device, thereby enhancing the ability to deploy and place the device within the vasculature, an issue of considerable importance if neither balloon nor mechanical placement methods are to be used. Furthermore, the invention can be arranged in a variety of configurations which allow overlapping of the circumferential and longitudinal elements to create particularly desired characteristics to the device and the placement capabilities thereof.

In a second presently preferred embodiment, the device may be configured so that a plurality of wires are used as described above to create more complex configurations and thereby enhance specific aspects of circumferential loop density or longitudinal portion pushability for various applications. Similarly, in another presently preferred embodiment, the density of loops can be varied from proximal to distal end in order to provide a relatively greater circumferential loop density in an area to be placed in a portion of the vasculature which is particularly weak or is threatened by treatment. In yet another presently preferred embodiment, the device may be configured to have a variable diameter to the circumferential elements over the length of the device in order to provide relatively greater circumferential tension against the wall of the vessel in some areas than others.

In another presently preferred embodiment, the present invention provides for an intravascular flow modifier and vascular reinforcement device with an elongate strand of resilient material having first and second proximal ends respectively connected by first and second legs of the elongate strand of resilient material to a distal continuous middle loop of the elongate strand of resilient material. The first and second proximal ends are preferably joined to a deployment device, with the first and second legs of the elongate strand of resilient material forming a double strand of a plurality of sinusoidal loops having upper and lower arcs. The sinusoidal loops preferably extend along a longitudinal axis intersecting the deployment device, with the upper and lower arcs of the sinusoidal loops being curved about the longitudinal axis to form a generally hollow cylindrical circumferential pattern of loops about the longitudinal axis. Two or more of the elongate strands can also be joined to the deployment device. In one variant, each of the first and second legs have proximal, intermediate and distal regions, with the proximal and distal regions of the first and second legs of sinusoidal loops being more tightly coiled than the intermediate regions of the first and second legs of sinusoidal loops to thereby provide a greater contact surface area for anchoring of the proximal and distal regions within a vessel. The proximal and distal regions of the first and second legs of sinusoidal loops may alternatively, or additionally, have a larger diameter than the intermediate regions of the first and second legs of sinusoidal loops to thereby provide a greater radial contact force for anchoring of the proximal and distal regions within a vessel. The intermediate regions of the first and second legs of sinusoidal loops can optionally be provided with squared sinusoidal loops.

In another presently preferred embodiment, the intravascular flow modifier and vascular reinforcement device can further be provided with an outer covering formed from a covering material selected from the group consisting of polyethylene terephthalate, polytetrafluoroethylene, polyamide, such as nylon, polyurethane, and liquid crystal polymer. The outer covering material can be formed as a fiber, and can be woven, or can be formed as a ribbon wound about the intravascular flow modifier and vascular reinforcement device. In another presently preferred aspect, the elongate strand of resilient material can be coated with a hydrophilic material.

In another presently preferred embodiment, the elongate strand of resilient material of the intravascular flow modifier and vascular reinforcement device further comprises one or more intermediate loops between the first and second legs and the distal middle loop, the one or more intermediate loops extending radially outward from the longitudinal axis in the expanded configuration so as to allow the one or more intermediate loops to extend into an aneurysm extending from the vessel. The one or more intermediate loops may be rounded or oval, for example.

The invention also provides for an apparatus for removing clots from the vasculature of a patient. The apparatus is formed from an elongate strand of resilient material having first and second proximal ends respectively connected by first and second legs of the elongate strand of resilient material to a distal middle loop of the elongate strand of resilient material, the first and second proximal ends being non-detachably joined to a deployment device, the first and second legs of the elongate strand of resilient material forming a double strand of a plurality of sinusoidal loops having upper and lower arcs, the sinusoidal loops extending along a longitudinal axis intersecting the deployment device, the upper and lower arcs of the sinusoidal loops being curved about the longitudinal axis, the elongate strand of resilient material being movable from an initial compressed configuration to an expanded configuration extending outwardly from the longitudinal axis to trap and hold clots within a vessel, the elongate strand of resilient material being adapted to be placed within the vessel of the patient when the elongate strand of resilient material is in the compressed configuration and removed from the vessel when the elongate strand of resilient material is in the expanded configuration, whereby clots trapped by the loops can be withdrawn from the vessel. In one presently preferred aspect, the upper and lower arcs of the sinusoidal loops form a hollow conical circumferential pattern of loops about the longitudinal axis in the expanded configuration.

Another advantage of the present invention is that it may be used in arteries up to renal size while still providing the benefits of placement without the use of balloons or mechanical expansions. One significant benefit in such an application is that the flow through the vessel is never fully occluded by the placement of the device of the invention, and it is possible to place the device from a free flow micro-catheter that is relatively small in diameter compared to the inside diameter of the blood vessel being treated.

While certain features of the invention and its use have been described, it will be appreciated by those skilled in the art that many forms of the invention may be used for specific applications in the medical treatment of deformations of the vasculature. Other features and advantages of the present invention would become apparent from the following detailed description taken in conjunction with the accompanying drawings, which illustrate by way of example, the principles of the invention.

BRIEF DESCRIPTION OF THE DRAWINGS

FIG. 9 is a side elevational view of an alternate preferred embodiment of the intravascular flow modifier and vascular reinforcement device formed from a single elongate strand of resilient material with sinusoidal loops.

FIG. 10 is an end view of the device of FIG. 9.

FIG. 11 is a side elevational view of an alternate preferred embodiment of the intravascular flow modifier and vascular reinforcement device formed from a double elongate strand of resilient material with sinusoidal loops.

FIG. 12 is an end view of the device of FIG. 11.

FIG. 13 is a side elevational view of an alternate preferred embodiment of the intravascular flow modifier and vascular reinforcement device formed from a triple elongate strand of resilient material with sinusoidal loops.

FIG. 14 is an end view of the device of FIG. 13.

FIG. 15 is a side elevational view of an alternate preferred embodiment of the intravascular flow modifier and vascular reinforcement device with more densely coiled proximal and distal loops.

DETAILED DESCRIPTION OF THE PREFERRED EMBODIMENTS

As shown in the exemplary drawings, which are provided for the purposes of illustration and not by way of limitation, the device of the present invention is designed to be deployed intravascularly without the necessity of balloons or other expansive elements and can be deployed from a micro-catheter directly into the area to be treated. The intravascular device of the present invention is particularly useful for treatment of damaged arteries incorporating aneurysms and the like, particularly those which are treatable by the use of embolic coils or other embolic devices or agents used to occlude the aneurysm. More particularly, the device of the invention is particularly well adapted to use with the types of catheters used to place such embolic coils in aneurysms, and the device may be used to reinforce the area in the vicinity of the aneurysm while allowing placement of one or more embolic coils through the gaps in the stent, while assisting in the retention of the embolic devices within the dome of the aneurysm.

Figure 1:
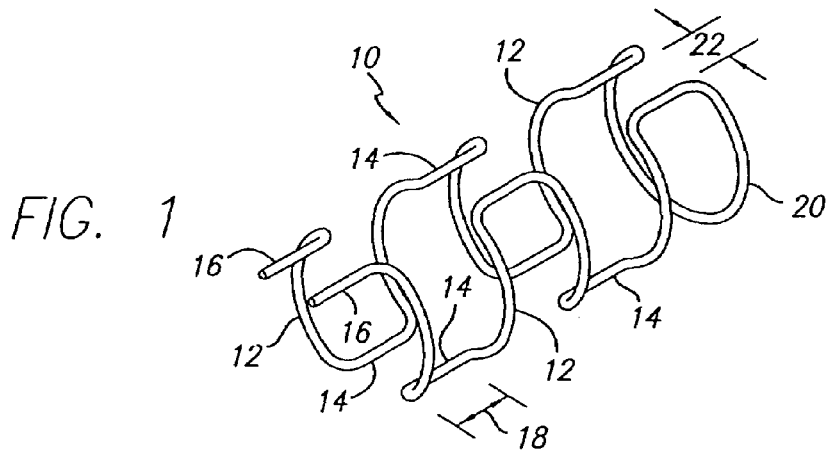
FIG. 1 is a perspective view of a deployed device configured according to the invention.

As illustrated in FIG. 1, one presently preferred embodiment of the present invention 10 can be configured as a series of circumferential loops 12 connected by longitudinal connecting sections 14 to progressively form an essentially cylindrical intravascular device 10 out of a single loop of wire. More specifically, the device is configured of a single piece of wire in which the free ends are placed in close proximity and a first linear section 16 extends axially, and in which the linear wire sections 14 are parallel and longitudinal with the ultimate approximately cylindrical configuration of the device. The wire is then formed into a pair of circumferential sections 12 extending in semi-circular arcs to a position in which a transition into a second pair of parallel elements 14 are formed for a second distance 18 at which they transition back to another pair of circumferential loops 12 and then proceeding sequentially in such a sequence towards an end loop 20 forming the end of the stent. While this configuration is described in the context of a wire, those skilled in the art will realize that other configurations of the material used to form the device, including foils and laminates, are within the scope of the invention. In the presently preferred embodiment, the wire of the device is made of a superelastic material such as a nickel titanium alloy to allow for easy insertion of the device within the micro-catheter. Other materials, such as shape memory alloys, may also be used to provide for the dual purposes of ease of insertion into the micro-catheter and formation upon deployment into the desired shape of the device. One material that is contemplated as a wire from which the device can be made is a stranded cable including one or more radiopaque strands, or which has radiopaque markers deployed along its length. Such a stranded cable can be made of a variety of materials including stainless steel, shape memory alloy, shape memory polymer, superelastic alloy, platinum or the like or combinations thereof.

The invention provides numerous important advantages in the treatment of vascular malformations, and particularly malformations which include the presence of aneurysms. Since the device does not represent an essentially solid tubular member, and does not require the use of a balloon or other mechanical device for deployment, it is capable of deployment from a micro-catheter which need not occlude the artery as it is put into a position from which to deploy the device. Furthermore, the device upon deployment can reinforce the artery without occluding access to the aneurysm, thus allowing the device to be deployed prior to the placement of embolic coils or the like in the aneurysms. Alternatively, depending on the nature of the vascular defect, the embolic coils or other embolic occlusive or other vasoocclusive devices can be placed and the device deployed thereafter to hold the devices in the aneurysm. By use of the invention, a variety of densities may be provided in the coil to coil distance, thus assisting in the treatment of different vascular malformations.

The present invention contains numerous advantages over the prior art, including enhanced pushability without creating circumferential stress from the loop section, as is often found in the case of coil-type intravascular flow modifiers known in the prior art. More specifically, the conformity of the device to the vascular walls is enhanced by the gaps in the loops 22 where the parallel sections are contained, and characteristics of the device such as loop strength and the resilience of the device are controlled by the radii 24 of the transitions to the longitudinal sections 14 the diameter of the wire and the distance between the parallel sections and the loops from which the device is formed. Thus, the invention provides a wide variety of performance characteristics that can be designed as part of the stent configuration.

Figure 2:
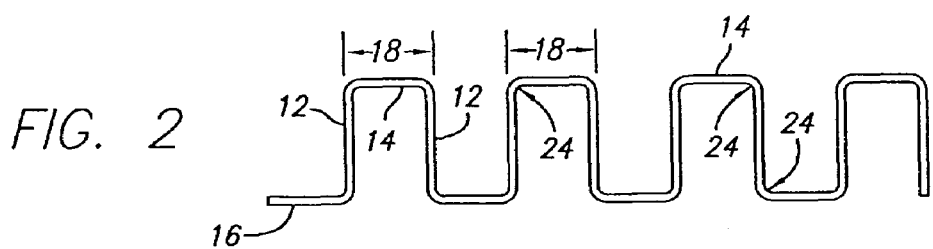
FIG. 2 is a side view of the deployed device of FIG. 1.
Figure 3:
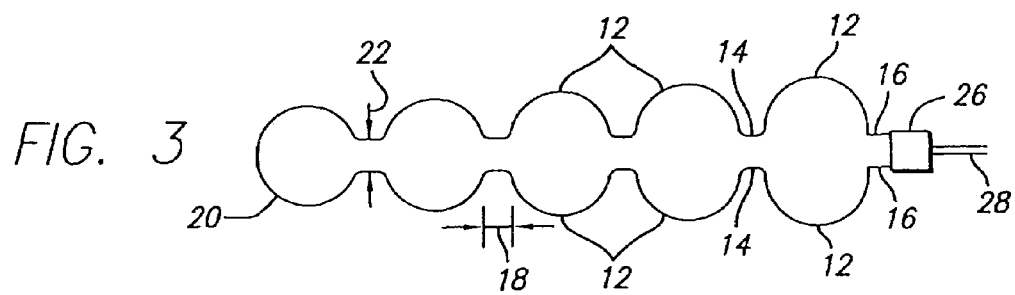
FIG. 3 is a plan view of a partially deployed device of the invention.
Figure 4:
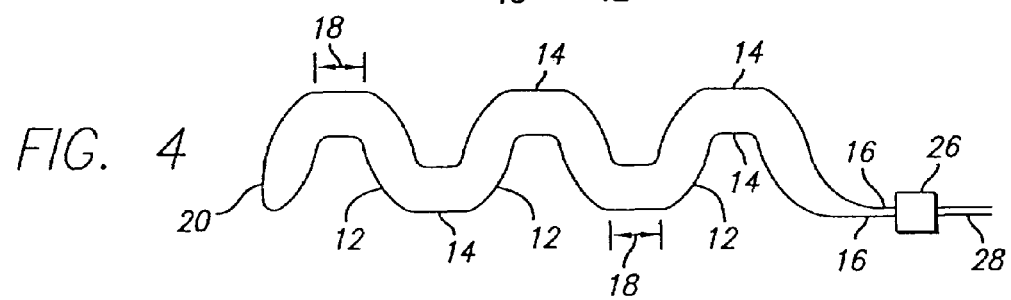
FIG. 4 is a side elevational view of the partially deployed device of FIG. 3.
Figure 5:
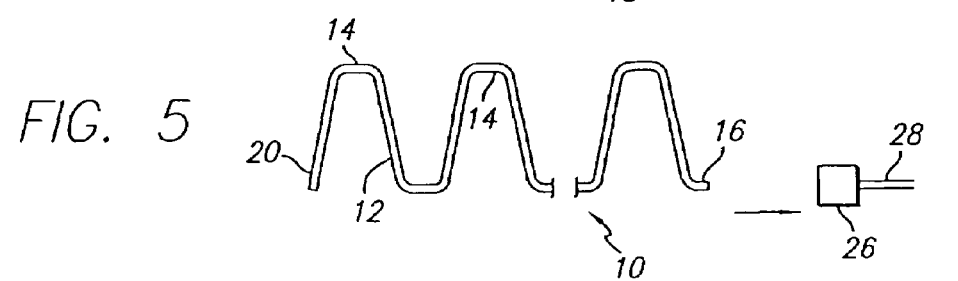
FIG. 5 is a side elevational view of the device showing the deployment connector being released from the device.

As shown in FIG. 2, the deployed device here illustrated in a side view, includes numerous longitudinal elements 14 and circumferential loops 12, the spacing of which can be varied as described above. As illustrated in FIG. 3, the device, prior to full deployment, can be made into an essentially flat configuration in which the free ends of the device are connected to the deployment device 26 on the distal end of a pusher 28 which fits within the micro-catheter (not shown). In this configuration, it can be seen that the circumferential loops 12 are connected by the short linear transitions 14 between the loops which become essentially parallel with the longitudinal axis of the device in the deployed configuration. FIG. 4 is an illustration of a partially deployed device in which the coils 12 have begun to assume their circumferential position within an artery. FIG. 5 illustrates the detachment of the device 10 from the distal end of the pusher 28 showing the device beginning to assume its final deployed position.

Figure 6:
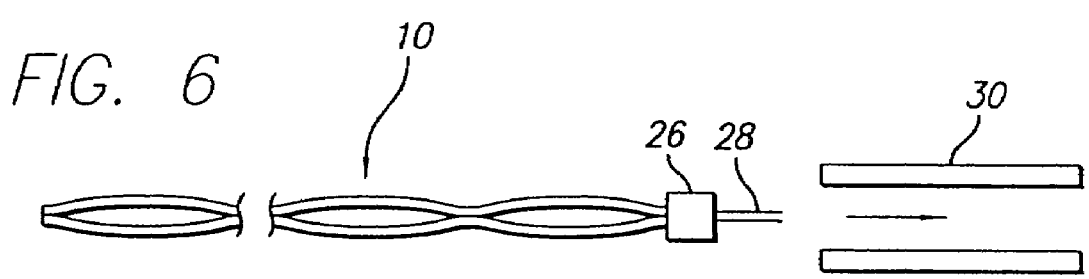
FIG. 6 is a top elevational view of the device configured for installation in a micro-catheter.

FIG. 6 illustrates the initial placement of the device 10 when made of superelastic or shape memory material in which it is first attached to the end of the pusher 28 and the pusher is then pulled into the micro-catheter 30, with the device assuming an essentially linear loop of wire that can then easily fit within the micro-catheter prior to deployment. Upon deployment, the pusher is used to extend the free end of the device from the micro-catheter in an area of the vasculature to be treated.

Figure 7:
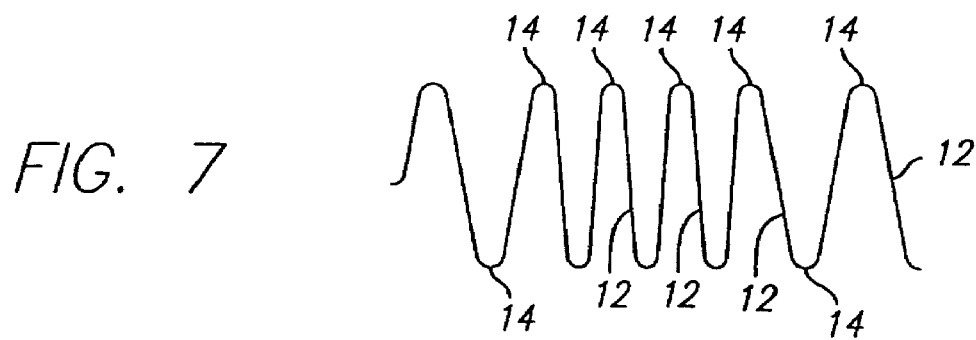
FIG. 7 is a side elevational view of a deployed device illustrating a second preferred embodiment in which the coil of the device are more densely located in the desired portion of the stent.

FIG. 7 illustrates one configuration of the device 10 of the present invention in which the device can be formed to have shorter connecting parallel sections 14 between the loops 12 and thus provide a higher degree of reinforcement in this specific area. Such a configuration has numerous benefits depending on the topology of the damage to the artery, and can provide benefits for certain types of treatment therapies.

Figure 8:
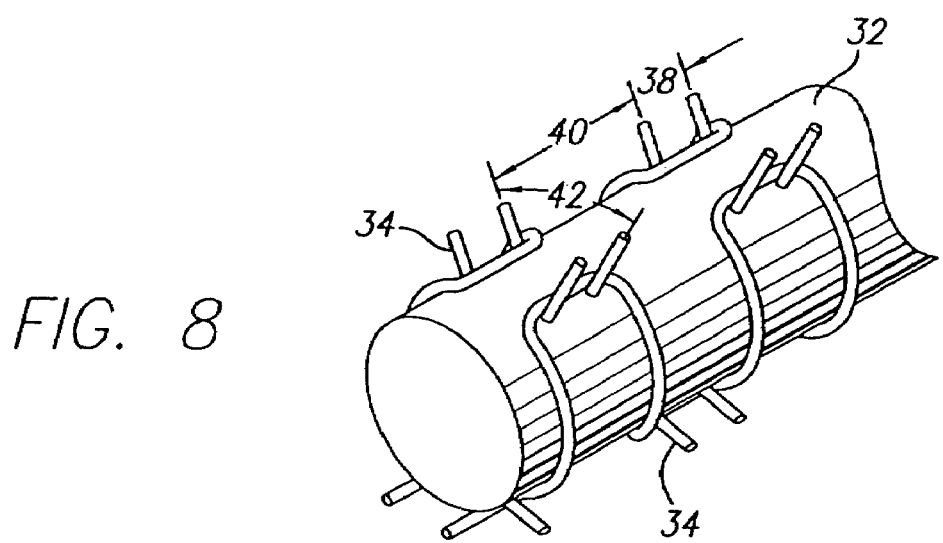
FIG. 8 is an illustration of a mandrel upon which the device is formed in one preferred embodiment of the method of manufacture of the device.

The present invention may be formed in a number of ways, but there are presently two preferred methods of manufacture. In a first preferred method illustrated in FIG. 8, a longitudinal mandrel 32 made of tungsten, ceramic or other heat resistant material has inserted into it pegs 34 of heat resistant material around which the wire to be formed into the device are wound. The diameter of the pegs 36 and the spacing of the pegs 38, 40, 42 may be altered in order to provide certain characteristics that are desired in the stent as it is formed. Alternatively, the mandrel can have a grooved configuration formed into it in which the wire is placed prior to heat treatment.

In another presently preferred embodiment illustrated in FIGS. 9 and 10, the present invention provides for an intravascular flow modifier and vascular reinforcement device 50 to be used in the intravascular treatment of blood vessels, with an elongate strand of resilient material 52 being formed to have first 54 and second 56 proximal ends respectively connected by first 58 and second 60 legs of the elongate strand of resilient material to a distal continuous middle loop 62 of the elongate strand of resilient material. The first and second proximal ends are preferably joined to a deployment device 64, with the first and second legs of the elongate strand of resilient material forming a double strand of a plurality of sinusoidal loops 66 having upper 68 and lower 70 arcs. The sinusoidal loops preferably extend along a longitudinal axis 72, the upper and lower arcs of the sinusoidal loops being curved about the longitudinal axis to form a hollow cylindrical circumferential pattern of loops about the longitudinal axis. In another presently preferred aspect illustrated in FIGS. 11 and 12, two of the elongate strands 74 can be joined to the deployment device, and in another presently preferred aspect illustrated in FIGS. 13 and 14, three or more of the elongate strands 76 can be joined to the deployment device.

Figure 16:
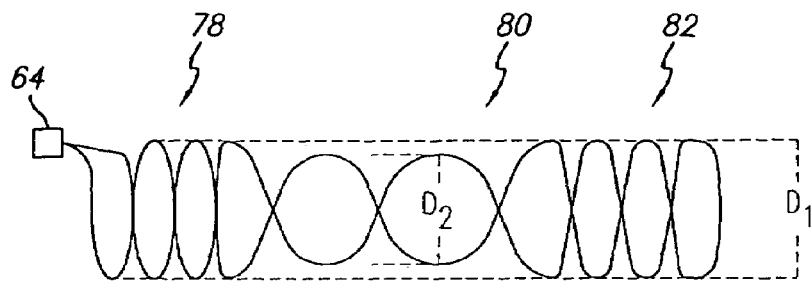
FIG. 16 is a side elevational view of an alternate preferred embodiment of the intravascular flow modifier and vascular reinforcement device with proximal and distal loops having a larger diameter.
Figure 17:
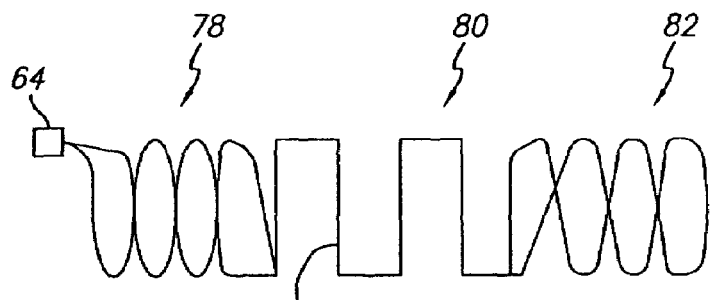
FIG. 17 is a side elevational view of an alternate preferred embodiment of the intravascular flow modifier and vascular reinforcement device with intermediate squared sinusoidal loops.

As is shown in FIG. 15, in a first presently preferred modification of the embodiments of FIGS. 9 to 14, each of the first and second legs have proximal 78, intermediate 80 and distal 82 regions, with the proximal and distal regions of the first and second legs of sinusoidal loops being more tightly coiled than the intermediate regions of the first and second legs of sinusoidal loops to thereby provide a greater contact surface area for anchoring of the proximal and distal regions within a vessel. Alternatively, as shown in FIG. 16, the proximal and distal regions of the first and second legs of sinusoidal loops may be provided with a larger diameter $D_1$ than the diameter $D_2$ of the intermediate regions of the first and second legs of sinusoidal loops to thereby provide a greater radial contact force for anchoring of the proximal and distal regions within a vessel. In another alternate preferred embodiment illustrated in FIG. 17, the intermediate regions of the first and second legs of sinusoidal loops can be provided with squared sinusoidal loops 84. As noted above, the elongate strand of resilient material can be made of a superelastic, shape memory material, such as a nickel-titanium alloy, or a shape memory polymer, and can be formed of a stranded cable.

Figure 18:
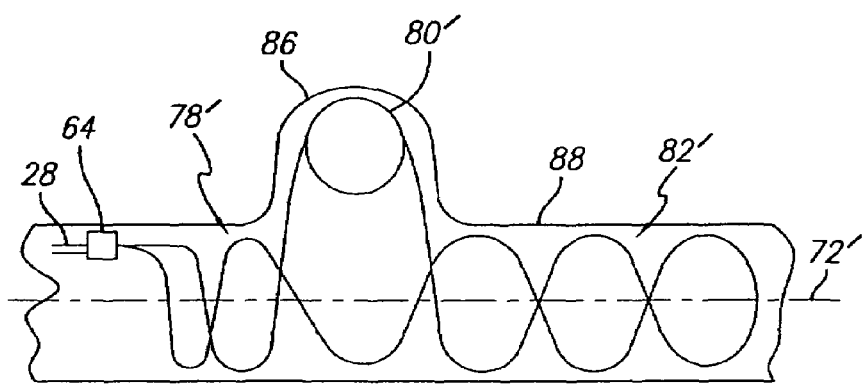
FIG. 18 is a side elevational view of an alternate preferred embodiment of the intravascular flow modifier and vascular reinforcement device formed with a rounded intermediate loop between the proximal and distal regions extending radially outward, shown deployed in a vessel with an aneurysm.
Figure 19:
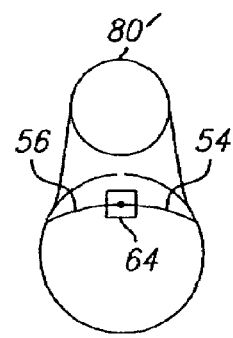
FIG. 19 is an end view of the device of FIG. 18.
Figure 20:
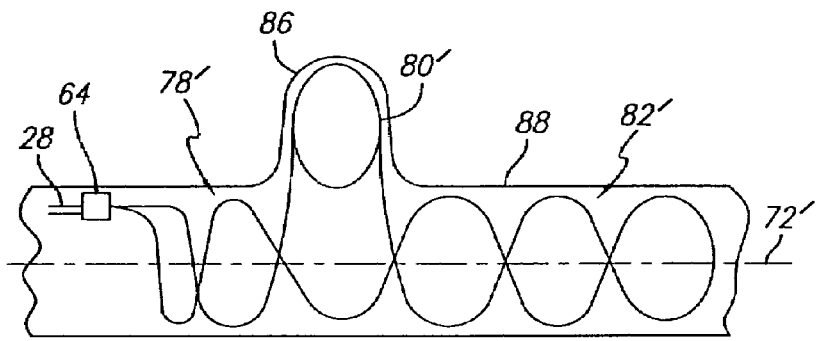
FIG. 20 is a side elevational view of an alternate preferred embodiment of the intravascular flow modifier and vascular reinforcement device formed with an oval shaped intermediate loop between the proximal and distal regions extending radially outward.

Referring to FIGS. 18 and 19, in another presently preferred embodiment, the one or more intermediate loops 80' of the elongate strand of resilient material of the intravascular flow modifier and vascular reinforcement device between the proximal 78' and distal 82' regions extend radially outward from the longitudinal axis 72' beyond the circumference of the proximal and distal regions in the expanded configuration of the device so as to allow the one or more intermediate loops to extend into an aneurysm 86 extending from a vessel 88. In a presently preferred embodiment, a plurality of the intermediate loops 80' are provided. As is illustrated in FIG. 18, the one or more intermediate loops 80' are round, although the one or more intermediate loops may alternatively be oval shaped, as shown in FIG. 20. Other similar shapes of the intermediate loop region of the intravascular flow modifier and vascular reinforcement device, such as squared sinusoidal loops similar to those shown in FIG. 17, but extending outwardly from the longitudinal axis beyond the circumference of the proximal and distal loops, may also be suitable.

Figure 21:
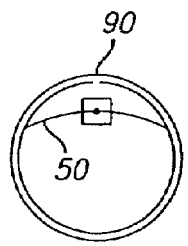
FIG. 21 is an end view of the intravascular flow modifier and vascular reinforcement device provided with an outer covering.
Figure 22:
FIG. 22 is a side elevational view of the intravascular flow modifier and vascular reinforcement device provided with an outer covering formed as a ribbon wound around the intravascular flow modifier and vascular reinforcement device.

Referring to FIG. 21, in another presently preferred embodiment, the intravascular flow modifier and vascular reinforcement device 50 can further be provided with an outer covering 90 formed from a covering material such as a polyester such as polyethylene terephthalate (PET), also available under the trade mark "DACRON", polytetrafluoroethylene (PTFE) also available under the trade mark "TEFLON", polyamide, such as nylon, polyurethane, or liquid crystal polymer, although other similar materials may also be suitable. The outer covering can be formed from a fiber of the covering material, and can be woven, or as shown in FIG. 22, the outer covering 90 can be formed as a ribbon of the covering material wound about the intravascular flow modifier and vascular reinforcement device.

Figure 23:
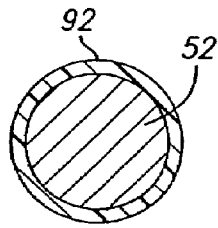
FIG. 23 is a cross-sectional view of the elongate strand of resilient material of the intravascular flow modifier and vascular reinforcement device provided with an outer coating of hydrophilic material.

In another presently preferred aspect, as is illustrated in FIG. 23, the elongate strand of resilient material can include an outer coating 92 of a hydrophilic material. The hydrophilic material can be a hydrogel, for example, which is typically formed by polymerization and crosslinking of a hydrophilic monomer in an aqueous solution to cause the solution to gel. For example, the hydrophilic material can be an organic gel, an inorganic gel, or a combination of two or more of such gels. Organic gels from which the hydrogel of the invention can be selected include, by way of example and not by way of limitation, gels formed from polysaccharides and mucopolysaccharides including, but not limited to hyaluronic acid, dextran, heparin sulfate, chondroitin sulfate, heparin, agar, starch, and alginate; polyaminoacids; proteins that support cell growth and healing, including but not limited to fibronectin, gelatin, collagen, fibrin, pectins, albumin, ovalbumin, and polyamino acids; collagen-hydroxyethyl-methacrylate (HEMA); polyphosphazines; polyphosphoesters; polyethylene glycol; polyethylene oxide; polyvinyl alcohol; polyvinylpyrrolidone; polyethyloxazoline; polyethylene oxide-co-polypropyleneoxide block copolymers; PGA-PEG-PGA block copolymers; PGA-PEG diblock copolymers; acrylates, including but not limited to diacrylates, oligoacrylates, methacrylates, dimethacrylates and oligomethoacrylates; PEG-oligoglycolylacrylates, such as described in U.S. Pat. No. 5,626,863, which is incorporated by reference herein; carboxy alkyl celluloses, including but not limited to carboxymethyl cellulose; partially oxidized cellulose; biodegradable polymers including but not limited to polymers and oligomers of glycolide, lactide, polylactic acid, polyesters of α-hydroxy acids, including lactic acid and glycolic acid, such as the poly(α-hydroxy) acids including polyglycolic acid, poly-DL-lactic, poly-L-lactic acid, and terpolymers of DL-lactide and glycolide; ε-caprolactone and ε-caprolactone copolymerized with polyesters; polylactones and polycaprolactones including poly(e-caprolactone), poly(d-valerolactone) and poly(gamma-butyrolactone); polyanhydrides; polyorthoesters; other hydroxy acids; polydioxanone; and other biologically degradable polymers that are non-toxic or are present as metabolites in the body; as well as non-degradable polymers such as styrene and acrolein.

Collagen-hydroxyethyl-methacrylate (HEMA) hydrogel polymer is commonly formed from a gelled and crosslinked hydrophilic monomer solution to form a three dimensional polymeric meshwork anchoring macromolecules. Crosslinking of the hydrophilic monomer solution can be accomplished by free radical polymerization of hydrophilic monomers, such as hydroxyethyl-methacrylate (HEMA). Hydrogel polymers formed by free radical polymerization of monomer solutions require crosslinking to form the three dimensional network to gel the aqueous solution. HEMA monomer solutions typically can be crosslinked to gel by dimethacrylate, although other crosslinking agents, such as ethylene glycol dimethacrylate or methylmethacrylate, can also be used during polymerization to modify the hydrogel. A wide variety of other hydrophilic monomers may also be suitable for purposes of the invention.

Inorganic gels from which the hydrophilic material of the invention can be selected include, by way of example and not by way of limitation, silica, alumina, and ferric oxide. It should thus be apparent that the hydrophilic material can be of a type that dissolves over time or that remains as a permanent coating of the elongate strand of resilient material.

Figure 24:
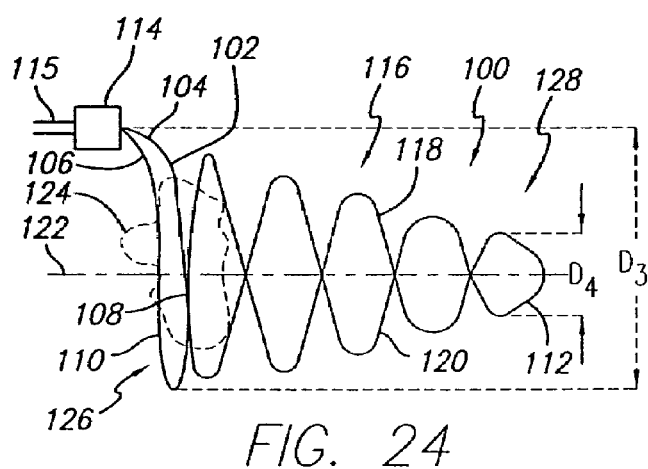
FIG. 24 is a side elevational view of an alternate preferred embodiment of a clot retrieval apparatus formed in a conical shape from an elongate strand of resilient material with sinusoidal loops.
Figure 25:
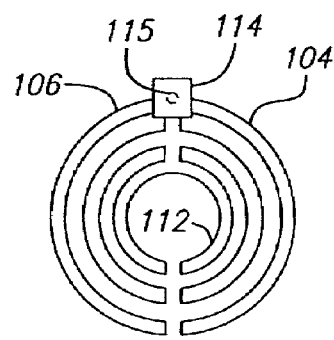
FIG. 25 is an end view of the device of FIG. 24.

With reference to FIGS. 24 and 25, the invention also provides for an apparatus 100 for removing clots from the vasculature of a patient. The apparatus is formed from an elongate strand of resilient material 102 having first 104 and second 106 proximal ends respectively connected by first 108 and second 110 legs of the elongate strand of resilient material to a distal continuous middle loop 112 of the elongate strand of resilient material. The first and second proximal ends are preferably non-detachably joined to a deployment device 114 connected to a pusher member 115, with the first and second legs of the elongate strand of resilient material forming a double strand of a plurality of sinusoidal loops 116 having upper 118 and lower 120 arcs. The sinusoidal loops preferably extend along a longitudinal axis 122 intersecting the deployment device, the upper and lower arcs of the sinusoidal loops being curved about the longitudinal axis to form a hollow circumferential pattern of loops about the longitudinal axis. The elongate strand of resilient material is movable from an initial compressed configuration, such as that shown in FIG. 6, to an expanded configuration shown in FIGS. 24 and 25, extending outwardly from the longitudinal axis to trap and hold one or more clots 124 within a vessel. In a presently preferred aspect, a plurality of the elongate strands of resilient material are joined to the deployment device to form a plurality of loops.

The elongate strand of resilient material is thus adapted to be placed within a vessel of the patient when the elongate strand of resilient material is in the compressed configuration, such as through a micro-catheter beyond a clot to be retrieved, and withdrawn and removed from the vessel when the elongate strand of resilient material takes on the expanded configuration, whereby clots trapped by the loops can be withdrawn from the vessel. In one presently preferred aspect, illustrated in FIGS. 24 and 25, the upper and lower arcs of the sinusoidal loops form a hollow conical circumferential pattern of loops about the longitudinal axis in the expanded configuration, in which the proximal region 126 of the first and second legs of sinusoidal loops tapers from a larger diameter $D_3$ to a smaller diameter $D_4$ of the distal region 128 of the loops to provide multiple filtering loops for collection and retrieval of clots from a vessel. Alternatively, device may have an expanded conical configuration in which the proximal region of the loops tapers from a smaller diameter to a larger diameter distal region of loops. Other similar configurations of varying diameters of loops may also be suitable for providing multiple filtering loops for collection and retrieval of clots from a vessel.

From the above, it may be seen that the present invention provides significant benefits to the treatment of vascular malformations, and particularly aneurysms in the neurovasculature. Importantly, the invention is particularly advantageous when used in combination with vasoocclusive devices placed in the aneurysm by intravascular procedures.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An intravascular flow modifier and vascular reinforcement device to be used in the intravascular treatment of blood vessels, comprising:

an elongate strand having first and second proximal ends respectively connected by first and second legs of the elongate strand to a distal middle loop of the elongate strand, said first and second proximal ends being joined to a deployment device, said first and second legs of the elongate strand forming a plurality of sinusoidal loops having first and second opposing arcs, said sinusoidal loops extending about a longitudinal axis of said intravascular flow modifier and vascular reinforcement device, said first and second opposing arcs of said sinusoidal loops being curved about said longitudinal axis to form a hollow cylindrical pattern of substantially symmetrical loops about said longitudinal axis.

2. The intravascular flow modifier and vascular reinforcement device of claim 1, wherein a plurality of said elongate strands are joined to said deployment device.

3. The intravascular flow modifier and vascular reinforcement device of claim 1, wherein each of the first and second legs have proximal, intermediate and distal regions, said proximal and distal regions of said first and second legs of sinusoidal loops being more tightly coiled than said intermediate regions of said first and second legs of sinusoidal loops to thereby provide a greater contact surface area for anchoring of said proximal and distal regions within a vessel.

4. The intravascular flow modifier and vascular reinforcement device of claim 1, wherein each of the first and second legs have proximal, intermediate and distal regions, said proximal and distal regions of said first and second legs of sinusoidal loops having a larger diameter than said intermediate regions of said first and second legs of sinusoidal loops to thereby provide a greater radial contact force for anchoring of said proximal and distal regions within a vessel.

5. The intravascular flow modifier and vascular reinforcement device of claim 1, wherein each of the first and second legs have proximal, intermediate and distal regions, said intermediate regions of said first and second legs of sinusoidal loops having squared sinusoidal loops.

6. The intravascular flow modifier and vascular reinforcement device of claim 1, further comprising a substantially cylindrical outer covering around said intravascular flow modifier and vascular reinforcement device.

7. The apparatus of claim 1, said elongate strand further comprising at least one intermediate loop between said first and second legs and said distal middle loop, said at least one intermediate loop extending radially outward from said longitudinal axis in said expanded configuration so as to allow said at least one intermediate loop to extend into an aneurysm extending from the vessel.

8. The apparatus of claim 7, wherein said at least one intermediate loop has a rounded configuration in said expanded configuration.

9. The apparatus of claim 7, wherein said at least one intermediate loop has an oval configuration in said expanded configuration.

* * * * *